United States Patent [19]

Bonnet

[11] Patent Number: 4,595,023
[45] Date of Patent: Jun. 17, 1986

[54] APPARATUS AND METHOD FOR DETECTING BODY VIBRATIONS

[76] Inventor: Kenneth Bonnet, 111 S. Centre Ave., Rockville Center, N.Y. 11570

[21] Appl. No.: 654,986

[22] Filed: Sep. 27, 1984

Related U.S. Application Data

[63] Continuation-in-part of Ser. No. 321,804, Nov. 16, 1981, abandoned, which is a continuation of Ser. No. 68,610, Aug. 22, 1979, abandoned.

[51] Int. Cl.$^4$ .............................................. A61B 5/10
[52] U.S. Cl. .................................... 128/782; 128/721
[58] Field of Search ................ 128/774, 782, 721–722, 128/714–715, 687

[56] References Cited

U.S. PATENT DOCUMENTS

| 3,090,226 | 5/1963 | Corti et al. ...................... 128/782 X |
| 3,465,747 | 9/1969 | Rogallo ................................ 128/714 |
| 3,494,329 | 2/1970 | Frieberger et al. ............. 128/782 X |
| 3,658,052 | 4/1972 | Alter .................................... 128/721 |
| 3,826,145 | 7/1974 | McFarland ........................ 128/782 |
| 3,890,958 | 6/1975 | Fister et al. ...................... 128/714 |
| 3,945,373 | 3/1976 | Tweed et al. ..................... 128/782 |

FOREIGN PATENT DOCUMENTS 0123284  2/1959  U.S.S.R. .............................. 128/714

*Primary Examiner*—Edward M. Coven
*Assistant Examiner*—Angela D. Sykes
*Attorney, Agent, or Firm*—Arthur T. Fattibene

[57] ABSTRACT

An apparatus and method are provided for detecting body vibrations of a living animal or human being, such as those generated by heart function and respiration. The system employs a rigid spring-like structure formed of one or more deflectable elements such as metal or plastic strips or a strip-like formation, preferably configured in a sinuous or irregular path and supported at one or more locations along its length by a support, such as a frame forming the wall of a container such as the bottom of a bassinet or other container. In one form, the irregularly shaped deflectable member or members are disposed to be directly engaged by an animal lying thereon, for testing purposes. In another form, a sheet of plastic is disposed across the deflectable member or members on the upper surface of which a portion of the body of an animal or human being may lie or sit to permit body vibrations to be transmitted through the sheet to the deflectable member and to be detected when such member deflects. The vibrational energy transmitted to the deflectable member is conducted therefrom through a centrally disposed rod or pin to a transducer, such as an audio speaker, which transduces the vibrational energy to electrical signals which may be amplified and detected by a recording or indicating instrument.

20 Claims, 6 Drawing Figures

APPARATUS AND METHOD FOR DETECTING BODY VIBRATIONS

RELATED APPLICATIONS

This is a continuation-in-part of Ser. No. 321,804 filed Nov. 16, 1981, abandoned, which is a continuation of Ser. No. 068,610 filed Aug. 22, 1979, abandoned.

SUMMARY OF THE INVENTION

This invention relates to an apparatus and method for detecting vibrations, such as vibrations generated by a pulmonary function such as heartbeat or respiration of an animal or human being. The apparatus is particularly associated with either a container such as a bassinet or other container for a living being or a device on which such a container may be disposed provided that the body vibrations or sounds of the living animal are not absorbed by the components of the device but may be transmitted directly therethrough to the detection means. As a result, electrical signals are generated by a detector which are either directly indicative of or contain components which are indicative of such physiological functions as heartbeat and respiration which are directly associated with the living function of the subject being monitored. By applying suitable electrical analyzing or computer techniques, living beings such as animals or babies may be constantly or intermittently monitored as to such functions to determine their physical characteristics and, in one instance, to provide a means for detecting abnormal variations in such variables as heartbeat and respiration rate whereby if the abnormal functions are such as to indicate severe illness or a condition whereby immediate medical attention will be required, such attention may be rendered to correct the abnormal condition and, in certain instances, to prevent death or severe damage to the vital organs of the living being.

Various systems have been proposed for monitoring human and animal physiological functions. These have included systems which employ electrodes which are either implanted within the tissue of a living animal or are part of a transducer which is strapped against a portion of the body or limb of a living animal. Such detectors are obviously cumbersome and limit ambulation of the subject being monitored. In contradistinction, the instant invention employs an external detection system for body vibrations and sounds which does not limit movement of the subject being monitored and does not require the attachment of any kind of device to the body of the patient or subject. As a result, the subject may move and leave the vicinity of the detection device without restriction and without the usual inconvenience and hazards associated with body attached sensors or detectors.

Accordingly it is a primary object of this invention to provide a new and improved apparatus and method for detecting physiological functions of a living animal or human being while reclining or sitting and without the use of sensors connected directly to or disclosed against the body of the subject being monitored.

Another object is to provide a system amd method for detecting human body vibrations, such as heartbeat and respiration, and generating electrical signals indicative of same, which signals may be processed and utilized to automatically and continuously monitor the conditions of the living being under observation.

Another object is to provide an apparatus and method for detecting heartbeat of an infant or a small animal, without the necessity of connecting devices to the body of the subject.

Another object is to provide a detection and alarm system particularly useful for monitoring heart rate of an infant, which system includes electronic control means for operating an alarm when the heartbeat drops below and/or increases above respective pre-set limits.

Another object is to provide an electronic detection system for detecting abnormal heart functions of a living being, which function is related to heartbeat rate, and for indicating when such function varies beyond a given limit or limits.

Another object is to provide an apparatus and method for performing psychological and physiological experiments on small laboratory animals in which reactions to variations in ambient condition, such as shocks, are detected and monitored wherein the detection means is also employed to apply electrical shocks to the subject being tested and monitored.

With the above and such other objects in view as may hereafter more fully appear, the invention consists of the novel constructions, combinations and arrangements of parts as will be more fully described and illustrated in the accompanying drawings but it is to be understood that changes, variations and modifications may be resorted to which fall within the scope of the invention as claimed without departing from the spirit and nature of the invention.

Figure 1:
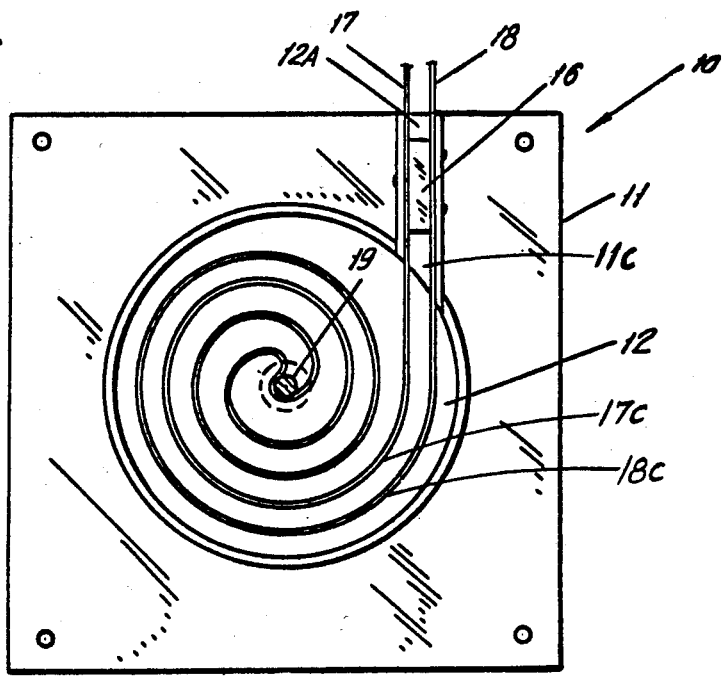
FIG. 1 is a plan view of a laboratory device which may be used to detect tremors, heartbeat and respiration of living animals such as mice, guinea pigs and the like under certain controlled conditions and conditions of stress.

In FIG. 1 is shown a first form of the invention defined by an apparatus 10 for determining physiological variables of a laboratory animal, such as a rat or other rodent on which experiments are to be performed such as reaction to shock, stress and other environmental variables. The apparatus 10 is formed of a pair square plates 11 and 14 made of plastic or metal and having aligned circular central openings 12 and 15 and supported on four vertical legs 13 secured by fasteners or other means to the corners thereof for supporting said platform a distance above a surface S such as a tabletop. Circular opening 12, provided in the center of platform 11 defines the space in which a spring-like member may be disposed for supporting an animal thereon. A channel 11C is formed in the upper surface of the plate 11 and extends from an edge thereof, substantially tangential to the circular opening 12. Disposed within an extending along the channel 11C are two stainless steel strips 17 and 18 extending parallel and space separated from each other. Each of such strips is formed in a respective flat coil or spiral formation, denoted 17C and 18C, which formations are disposed within the circular opening 12 and spiral toward the center of the opening. At the center of the coils of strips 17 and 18 and joining them together, is a metal rod or pin 19 to which the ends of strips 17 and 18 are welded or fastened, which rod serves as a vibration coupling means which extends vertically downward from the center of the two coils with the lower end 20 of rod 19 engaging a transducer 22, such as a small loud speaker or other force-to-electrical energy signal modulating transducer of suitable sensitivity. If such a loud speaker is used, the lower end of the rod 19 is disposed in engagement with the center of the speaker, such as the central portion of the diaphragm or the coil at the center of the speaker so that forces or vibrations transmitted to the rod are transmitted thereby to the speaker causing its diaphragm to vibrate or move longitudinally so that a variable current or analog signal will be induced in the coil thereof as it moves with respect to the fixed permanent magnet of the speaker. The output of the speaker coil is thus an electrical signal which varies in accordance with movement of the speaker diaphragm and coil effected by the movement of the rod 19, which movement varies in accordance with tremors or vibrations transmitted thereto through the spring-like coil or coils connected to the rod.

A small animal may be disposed on the flat coils 17C and 18C formed of the strips 17 and 18 and disposed across the opening 12 in the plate 11. Such body vibrations as caused by heartbeat, breathing, muscle contractions and expansions and other movements may be detected by detecting the variations in the current generated by the speaker coil as it moves longitudinally with respect to the permanent magnet of the speaker. The strips 17 and 18 may also be connected in a parallel electrical circuit in which the source of electrical energy may be selectively applied thereto and to the body of a laboratory animal extending across the coil formations of the parallel strips disposed within the circular opening 12 to permit experiments to be performed which are indicative of the reaction of the animal to variations in its environment including electrical energy applied to the parallel strips 17 and 18.

Notation 21 refers to a conical shield secured at its narrow end to a point near the lower end of the rod 19 while the conical portion thereof extends above and across the speaker or transducer 22 to protect the latter from contamination by body fluids and waste of the animal supported on the coils 17C and 18C. As indicated, the transducer 22 may comprise a small audio speaker or other suitable force-to-electrical signal generating device having its output lines or wires 27 connected directly to a device which may include an amplifier and a recorder, such as a strip chart recorder, signal processor and/or short wave transmitter of the signal information received.

Notation 19 refers to a glass tube, the lower end of which is supported by the upper surface of the plate 11 permitting such glass tube to circumscribe the opening 12 therein to maintain the laboratory animal disposed across the opening against the flat spiral formations of the strips 17 and 18.

Figure 2:
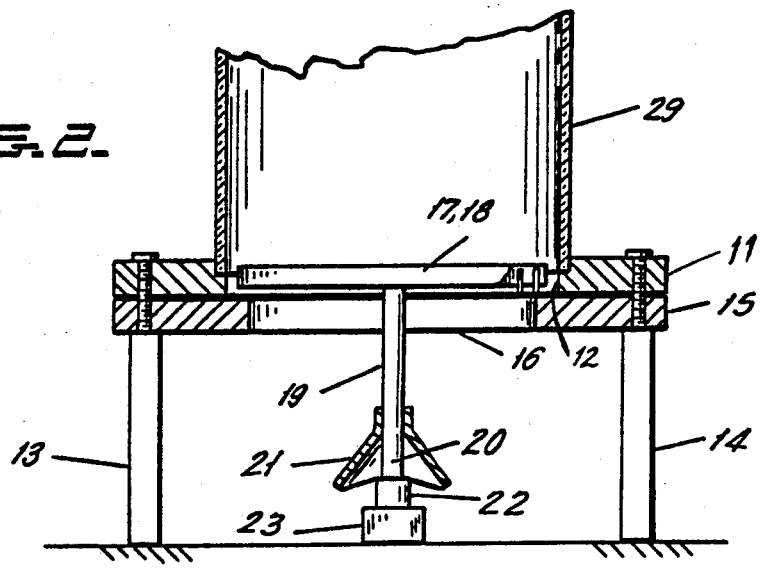
FIG. 2 is a side view of the lower portion of the apparatus of FIG. 1 with parts broken away for clarity.
Figure 3:
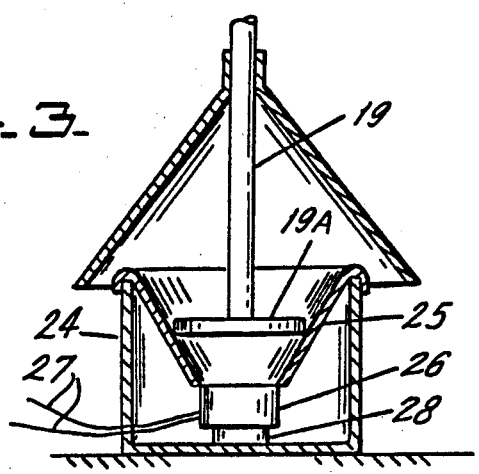
FIG. 3 is a side view with parts sectioned for clarity showing further details of a vibrations detector provided in FIG. 2.

Whereas in FIG. 2 the transducer 22 is shown supported on a base 23 which is secured to the upper surface S of a table or mount for the apparatus 10, in FIG. 3 the housing 24 for the transducer or speaker is supported directly on surface S and supports the outer rim of the speaker diaphragm or cone 25. A rigid disc 19A is secured to the end of the rod or dowel 19 and compressively engages a portion of the inside surface of the speaker cone 25 a short distance away from the small end of the speaker cone which supports the electromagnetic coil 26 of the speaker. Notation 27 refers to the lead wires extending from the speaker coil 26 to a remote amplifier and recorder or indicator of vibrational energy applied to the speaker through the rod 19 from the coils 17 and 18 while notation 28 refers to the permanent magnet disposed within the coil 26 forming part of the speaker and operable to induce variations in current generated by the coil when it is moved longitudinally by the longitudinal movements of the cone 25 effected by vibrations imparted to the rod 19 by variations in body functions and tremors of the animal disposed on the coils 17 and 18.

Figure 4:
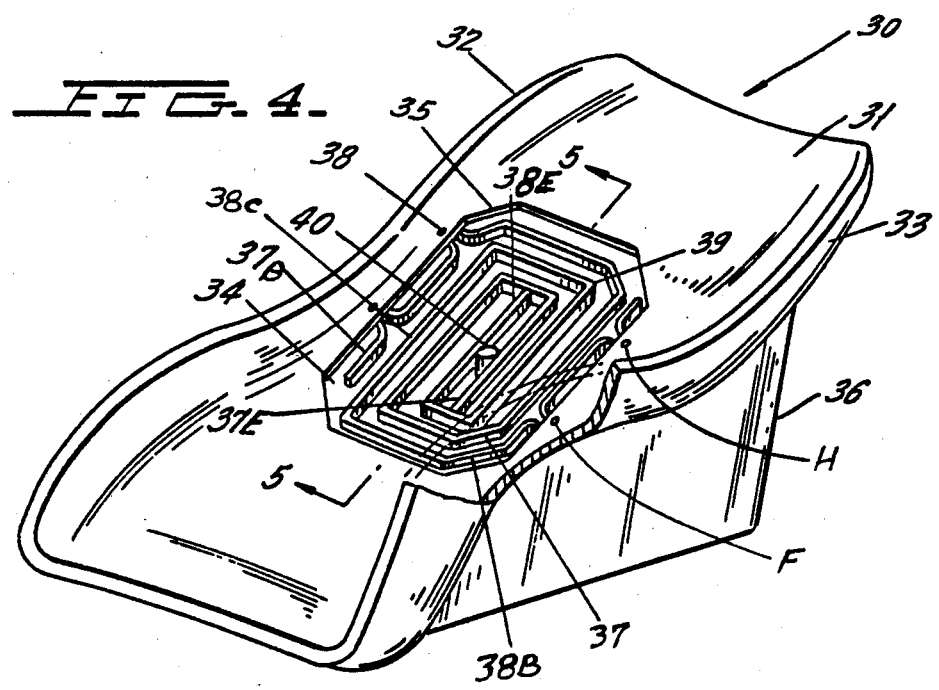
FIG. 4 is an isometric view with parts sectioned for clarity of an infant's retainer or bed containing heart beat and respiration detection means which is integrally assembled therewith.
Figure 5:
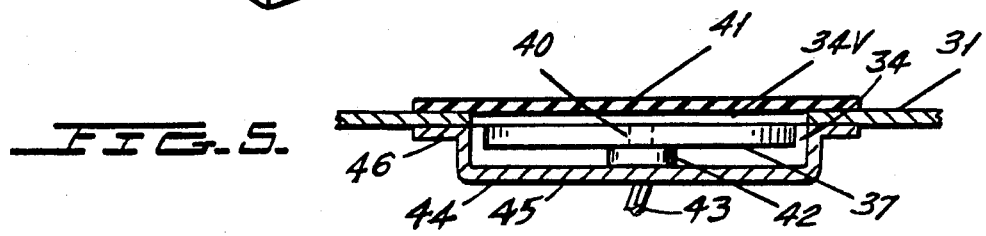
FIG. 5 is a side view in section of the portion of the retainer of FIG. 4 containing the detection means.

FIGS. 4 and 5 illustrate details of a support for an infant, such as a seat or inclined bed 30 having a central sheet-like portion 31 and integral shallow side walls 32 which portions are preferably molded of plastic together with a sheet-like support 36 for retaining the body supporting portion 31 inclined and upright on a surface, so that an infant placed on the upper surface 33 thereof will be retained in a comfortable position for sleeping. An opening 34 is provided in the center of the sheet-like portion 31 which opening is defined by a rim having a plurality of holes and bosses molded integral therewith for retaining the ends of a rectangular coil-like assembly of two strips 37 and 38 of stainless steel defining a coil spring for receiving body vibrations from the infant lying on the upper surface 33. The outer ends 37B and 38B of the coiled strips 37 and 38 are either drilled with holes for receiving fasteners passed through the holes H which are molded in the sheet-like portion 31 or are bent with loop-like formations through which the headed fasteners pass and hold said strips by means of respective nuts secured to the ends of the fasteners. The inner ends 37E and 38E of the strips 37 and 38 abut and are welded to respective inner portions of the opposite strips and support a pin or rod 40 therebetween which pin extends downwardly and engages a transducer 42, such as the cone of a microphone, as described, and as illustrated in FIG. 5. The transducer 42 is supported by the bottom wall 45 of a bracket or tray 44 which extends completely across the opening 34 defining a volume 34V beneath the infant supporting portion 31 in which volume the spring elements 37,38, the pin 40 and the transducer 42 are contained in proper assembly. Wires provided in an insulated cable 43 extend from the transducer 40 through a hole in the bottom wall 45 of the bracket 44 to a suitable monitor or alarm device for indicating, for example, when the infant's pulse rate has exceeded or fallen below given values. The flange or flanges 46 of the bracket or shallow tray 44 may be welded or secured with fasteners to the rim of wall 31. Extending across the opening 34 is a sheet 41 of suitable plastic which engages the upper surfaces of the coil elements so that the body vibrations of the infant will be transmitted therethrough to the spring-like elements 37,38 and to the transducer 42.

Figure 6:
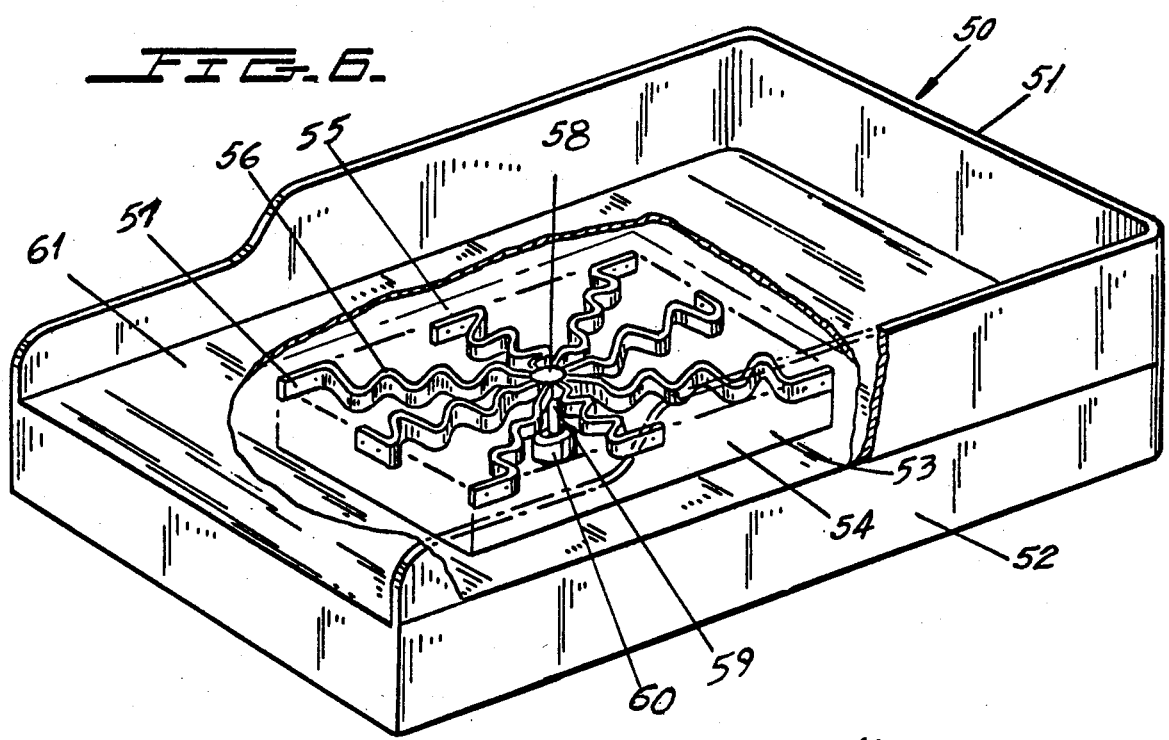
FIG. 6 is an isometric view of a bed or bassinet having body vibration and heart beat detection means supported in a container shown by sectioning the mattress of the bed.

In FIG. 6 is shown a modified form of the invention in which the desired physical variables of a person may be continuously monitored while such person is reclining, as in the act of sleeping or resting. The apparatus 50 includes a bed 51 and a mattress 52 with the central portion thereof removed of filler or springs and having an assembly 53 comprising a box-like container 54 with an upper flange 55 surrounding the side walls thereof and supporting a flexible pad or sheet extending across the open container. A plurality of components are supported within the container including a plurality of rigid strips 56 of stainless steel, each deformed in a sinuous or zig-zag configuration as shown and each extending from a location at the center of the container where they are joined together by means of a fitting 58. The flat ends 57 of each strip 56 join it to the respective side walls of the container to which each is connected by means of one or more fasteners. The fitting 58 supports a rod 59 which extends to and engages a force-to-electrical energy transducer 60, such as the described speaker, supported by the bottom wall of the container 53. The outer ends 57 of the spring-like members 56 are bent so as to permit each to flatly abut the respective side walls of the container 54 to permit such members to be fastened thereto. The fitting 58 is thus suspended at the center of the container by the plurality of spring-like elements 56. A flat pad or sheet 61 of flexible rubber or elastomeric resin, extends across the open upper end of the container and is secured to the flange 55 in a manner that such pad will compress against the upper edges of the formations 56 when a person is reclining on the bed or mattress 52.

The mat 52 preferably rests on a flat base such as a flat plywood board or other structure so that the bottom wall of the box-like container is supported thereby while the upper flange 55 thereof is at a level such that a person reclining on the bed or mattress will have suitable support for his body engaging the pad 61 and will thereby be operatively coupled to the spring-like members 56 in the box-like container 54 to permit body vibrations, such as those caused by heartbeat and respiration, to be transmitted through such spring-like elements, the fitting 59 and a portion thereof which normally bears against the transducer 60.

While electromagnetic means, such as a small loudspeaker, has been employed in the embodiments illustrated in the drawings and described above to transduce body vibrations imparted to the spring-like elements against which the bodies of human beings or animals are disposed, such as in reclining or sitting, other force transducers such as strain gauges, capacitance, piezoelectric or other type of force to electrical energy transducer may be employed which is engaged by the described coupling pin or rod extending from the cantilevered spring or coil.

One or more microphones may also be employed, which are supported by the support for the coil or spring to detect ambient noise which may be regularly or randomly generated in the vicinity of or remote from the detection pad or bed containing the vibration trnasducer. The signals generated on the output of such microphone may be applied to the same microprocessor or computer which processes and analyzes the signals output by the force transducer so as to account for same and permit the unwanted noise signals to be subtracted from the information signals defined by the body vibrations imparted to the spring or spring-like elements.

In a preferred form of the invention, the cantilevered spring like element or elements, such as elements 17 and 18 of FIG. 1, the stainless steel strips 37 and 38 of FIG. 4 and the strips 56 of FIG. 6 may comprise stainless steel tubing in the range of $\frac{1}{4}''$ to $\frac{1}{2}''$ in diameter which not only exhibits excellent vibrations transmission characteristics for transmitting the body vibrations described to the centrally located force transducer, but also provides an upper surface for receiving part of the weight of an infant or grown-up lying thereon or thereacross without discomfort.

I claim:

1. Body vibration sensing means comprising in combination:

a first support defining a body supporting portion adapted to be disposed beneath a living being to receive and support at least a portion of the weight of such living being, said body supporting portion having an opening adapted to be disposed beneath the portion of the weight of such living being not supported by said body supporting portion, spring means including at least one deflectable element which is cantileverily supported by said first support and extends into said opening in said body supporting portion of said first support in a manner to permit vibrational deflection of said deflectable element within said opening when body vibrations are imparted thereto from a living being supported above said body supporting portion, transducing means for sensing variations in force applied thereto and operable to indicate such force variations by means of a variable output signal, means for operatively coupling said deflectable element to said transducing means in a manner to permit the deflections of said deflectable element caused by variations in forces imparted thereto by a living being whose body is operatively coupled to said deflectable element to be sensed by said transducing means, and indicating means controlled by the signal output by said transducing means for indicating deflections of said deflectable element caused by vibrations imparted thereto.

2. An apparatus in accordance with claim 1 wherein said deflectable element has a narrow, strip-like configuration and is formed with an irregular shape.

3. An apparatus in accordance with claim 1 wherein said spring means comprises a strip-like deflectable element in the configuration of a flat spiral having outer and inner ends which deflectable element is supported at its outer end by said first support and is operatively coupled to said transducing means near its inner end.

4. An apparatus in accordance with claim 1 wherein said spring means comprises a strip-like deflectable element in the configuration of a substantially rectangular spiral.

5. An apparatus in accordance with claim 1 wherein said spring means has a narrow strip-like configuration and is formed with an irregular shape which is supported at two locations by said first support.

6. An apparatus in accordance with claim 1 wherein said transducing means includes a loud speaker and said means for operatively coupling said deflectable element to said transducing means comprises a rigid member secured to said deflectable element and engaging a portion of said speaker in a manner to impart vibration to said speaker when vibrations are imparted to said deflectable element by a living being.

7. An apparatus in accordance with claim 1 wherein said deflectable element and said means for operatively coupling said deflectable element to said transducing means define a unitary structure.

8. An apparatus in accordance with claim 1 wherein said deflectable element is formed of molded material.

9. An apparatus in accordance with claim 8 wherein said deflectable element and said means for coupling said deflectable element to said transducing means are integrally formed of a unitary molding.

10. An apparatus in accordance with claim 1 wherein said first support is in the configuration of at least a portion of a bed and a flexible sheet material is disposed across and engaging said deflectable element for receiving at least a portion of the weight of a living being reclining on said bed.

11. An apparatus in accordance with claim 1 wherein said first support forms part of a pad adapted to be disposed beneath a living being whose body vibrations are to be monitored thereby.

12. An apparatus in accordance with claim 1 wherein said support comprises a bassinet having a bottom wall containing said opening therein, said deflectable element being supported within said opening in said bottom wall at substantially the level of the bottom wall and a flexible sheet material extending across said opening and against said deflectable element to permit the weight of a baby disposed in said bassinet to bear against said deflectable element.

13. An apparatus in accordance with claim 1 in which said deflectable element is defined by two strip-like formations extending parallel to each other in a substantially flat spiral configuration.

14. An apparatus in accordance with claim 1 wherein said transducing means is a pressure transducer with a sensing element in sensing engagement with said spring means and operable to receive body vibrations transmitted to said spring means to generate variable electrical signals in accordance with variations in the vibrations received thereby.

15. An apparatus in accordance with claim 1 wherein said first support is in the configuration of a rigid frame.

16. An apparatus in accordance with claim 1 wherein said first support is in the configuration of a bed for supporting a living being reclining thereon.

17. An apparatus in accordance with claim 1 wherein said deflectable element is formed of stainless steel strip material.

18. An apparatus in accordance with claim 1 wherein said deflectable element is formed of stainless steel tubing.

19. An apparatus in accordance with claim 1 wherein said deflectable element is formed of stainless steel tubing having a diameter in the range of $\frac{1}{4}''$ to $\frac{1}{2}''$.

20. An apparatus in accordance with claim 1 including a plurality of deflectable elements secured together and operatively coupled to said transducing means.

* * * * *